(12) United States Patent
Boers et al.

(10) Patent No.: US 8,961,187 B2
(45) Date of Patent: Feb. 24, 2015

(54) PHANTOM

(75) Inventors: Frank Boers, Erkelenz (DE); Juergen Dammers, Juelich (DE); Heinz Rongen, Dueren (DE); Michael Schiek, Aachen (DE)

(73) Assignee: Forschungszentrum Juelich GmbH, Juelich (DE)

( * ) Notice: Subject to any disclaimer, the term of this patent is extended or adjusted under 35 U.S.C. 154(b) by 1592 days.

(21) Appl. No.: 12/449,332

(22) PCT Filed: Jan. 19, 2008

(86) PCT No.: PCT/DE2008/000089
§ 371 (c)(1),
(2), (4) Date: Aug. 31, 2009

(87) PCT Pub. No.: WO2008/098538
PCT Pub. Date: Aug. 21, 2008

(65) Prior Publication Data
US 2010/0047751 A1    Feb. 25, 2010

(30) Foreign Application Priority Data

Feb. 16, 2007    (DE) .......................... 10 2007 007 686

(51) Int. Cl.
G09B 23/28    (2006.01)
A61B 5/0476   (2006.01)
A61B 5/00     (2006.01)

(52) U.S. Cl.
CPC ............. A61B 5/0476 (2013.01); A61B 5/7207 (2013.01)
USPC ............................ 434/262; 434/270; 434/267

(58) Field of Classification Search
USPC .................................................. 434/267, 265
See application file for complete search history.

(56) References Cited

U.S. PATENT DOCUMENTS

| | | | |
|---|---|---|---|
| 5,099,144 A | | 3/1992 | Sai |
| 5,121,055 A | * | 6/1992 | Paulson et al. ................ 324/202 |
| 6,329,953 B1 | * | 12/2001 | McKivergan ................ 343/703 |
| 6,544,170 B1 | * | 4/2003 | Kajihara et al. ............. 600/300 |
| 7,190,301 B2 | * | 3/2007 | Krenz et al. ..................... 342/1 |
| 7,215,122 B2 | * | 5/2007 | Zhao et al. .................... 324/318 |
| 2004/0102694 A1 | * | 5/2004 | Iyama et al. .................. 600/410 |
| 2005/0228209 A1 | * | 10/2005 | Schneider et al. ............. 600/13 |
| 2006/0199159 A1 | * | 9/2006 | Ghiron et al. ................ 434/270 |
| 2007/0088211 A1 | * | 4/2007 | Cheng et al. .................. 600/410 |
| 2010/0185042 A1 | * | 7/2010 | Schneider et al. ............. 600/13 |
| 2010/0286470 A1 | * | 11/2010 | Schneider et al. ............. 600/14 |

FOREIGN PATENT DOCUMENTS

| | | |
|---|---|---|
| DE | 33 07 263 | 9/1984 |
| JP | 4-061844 | 2/1992 |
| JP | 2001-070272 | 3/2001 |

OTHER PUBLICATIONS

Leahy R M et al: "S study of dipole localization accuracy for MEG and EEG using a human skull phantom" Electroencephalography and Clinical Neurophysiology Elsevier Ereland, vol. 107, No. 2, Aug. 1998, pp. 159-173, XP002488488 ISSN: 0013-4694 the whole document.

(Continued)

*Primary Examiner* — Robert J Utama
(74) *Attorney, Agent, or Firm* — Jordan and Hamburg LLP

(57) ABSTRACT

A phantom comprises at least one first means for generating at least one dipole and at least one second means for actuating the first means in a non-electrical manner.

16 Claims, 2 Drawing Sheets

(56) References Cited

OTHER PUBLICATIONS

Friston K J: "Brain function, nonlinear coupling, and neuronal transients." The Neuroscientist : A Review Journal Bringing Neurobiology, Neurology and Psychiatry Oct. 2001, vol. 7, No. 5, Oct. 2001, pp. 406-418, XP002488489 ISSN: 1073-8584 cited in the application the whole document.

Spencer, M.E., et al., "A Skull-Based Multiple Dipole Phantom for EEG and MEG Studies", Proceedings of the 10th international conference on biomagnetism, S. 130-133, Biomag 96, Santa Fe, New Mexico, Feb. 1996.

Karl J. Friston, 2001. The Neuroscientist, vol. 7, No. 5, 406-418. SAGE Publications Brain Function, Nonlinear Coupling, and Neuronal Transients http://nro.sagepub.com.

Phillips, J.W., et al., "MEG-Based Imaging of Focal Neuronal Current Sources", IEEE Transactions on Medical Imaging, vol. 16, No. 3, W. 338-348, Jun. 1997.

\* cited by examiner

PHANTOM

BACKGROUND OF THE INVENTION

The invention relates to a phantom.

Electroencephalography, abbreviated EEG, is an important analysis method for characterizing brain activity. To this end, weak electrical currents accompanying brain activity are derived at defined points on the scalp using electrodes. The voltage fluctuations between two of these electrodes are amplified in each case and recorded by a multi-channel recorder as a function of time. The resulting electroencephalogram makes it possible to draw conclusions about brain diseases.

In contrast, magnetoencephalography, abbreviated MEG, is a measurement of the magnetic activity of the brain using external sensors, such as so-called superconducting quantum interference devices (SQUIDs). The magnetic signals in the brain are caused by the electrical currents in active nerve cells. As a result, a magnetoencephalograph can be used to record data that is an expression of the present overall activity of the brain, without time delay.

A magnetoencephalograph provides good spatial resolution and very high temporal resolution. Modern whole-head magnetoencephalographs have a helmet-like configuration, comprising, for example, approximately 300 magnetic field sensors, and this is placed on the head of the patient or test subject without contact during measurement. Since the magnetic signals in the brain amount to only a few femtotesla, outside interference must be shielded to as great an extent as possible.

The key advantages of magnetoencephalography, as compared to electroencephalography, are the easy application of the device, which provides both a large number of channels and precisely known sensor positions and, as a result of the measurement modality, the ability register the activities of deeper brain regions as well.

Recorded brain signals typically constitute a complex composition of many superimposed individual brain activities and also endogenous artifact signals, such as those of the cardiac activity and the eyes and facial muscles. Isolating and localizing the signals associated with the key brain activities from all the sensor signals that are determined, in order to be able to specifically analyze them, is a particular challenge of modern neuroscience.

A difficulty in terms of the localization of electrical currents by way of the magnetic fields measured by a magnetoencephalograph is non-uniqueness in the so-called inverse problem. In this problem, one and the same arbitrarily precisely measured magnetic field distribution may be generated by different arrangements of electrical current densities. Accordingly, limiting assumptions regarding the geometric distribution of the current densities are also required in order to localize the current densities based on the measured magnetic fields. The different back calculation algorithms are based on assumptions.

Different back calculation algorithms are known from Phillips (Phillips, J. W., Leahy, R. M., Mosher, J. C. (1997). MEG-based imaging of focal neuronal current sources. IEEE Transactions on medical imaging, Vol. 16, No. 3, 338-348).

The quality of back calculation algorithms for the localization and quantification of the current densities is ensured using artificially generated current density distributions. For this purpose, electrical or magnetic dipoles having defined intensities are generated in exactly defined local physical sites in a so-called phantom. A phantom, therefore, is a device for generating spatially distributed electromagnetic signals.

A head phantom for this purpose comprises, for example, an array of 32 current dipoles, a computer for controlling a 32-channel dipole driver, and the actual head phantom. Such a phantom is disclosed in the published prior art by Spencer et al. (Spencer, M. E., Leahy, R. M, and Mosher, J. C, 1996. A skull-based multiple dipole phantom for EEG and MEG Studies. Proceedings of the $10^{th}$ international conference on biomagnetism, Biomag '96, Santa Fe, N. Mex., February 1996).

An electrical dipole is generated in phantoms using a thin coaxial cable, which is actuated via a voltage source. The two contacts at the cable end are open in an electrically conductive medium within the phantom. If the ends are connected to each other by a wire, which is wound into a coil, a magnetic dipole can thus be generated. In this way, each coaxial cable forms a measurement site, and a dipole is generated at this exactly defined point when a voltage is applied. The dipole is sensed by external sensors.

A plurality of dipoles can be generated in the phantom using a corresponding number of spatially distributed coaxial cables, which are actuated electrically via a dipole driver.

A head phantom has a head-shaped configuration, in order to emulate the anatomy of a head. An electrically conductive medium at the interior of the phantom approximately emulates the electrical properties of the brain, in order to allow calibration of the data measured in a test subject on the basis of the data determined with the phantom.

With a phantom, variances in distributions reconstructed by way of the algorithms usually occur with respect to the actual distributions. The lower the variance is between the reconstructed parameters and the actual parameters, such as the intensity and localization of the distributions, the higher is the quality of the overall measurement system. The variances in the data for individual channels can be incorporated in an iterative optimization of the back calculation algorithm.

In order to sustainably improve the quality of the measurement system, the measurement of the current density distributions, or the magnetic field distributions, must be performed with as little interference as possible. To this end, the quality of the shields on the coaxial cables used will be higher or lower, depending on the requirements. Furthermore, in the phantom, it is possible to address only one channel at a time.

The disadvantage of this procedure is, however, that only a single dipole is thus generated at any one time in the phantom. The calibration of the measurement system is consequently comparatively time-consuming and complex problems cannot be simulated rapidly and realistically.

It is known from Friston (Karl J. Friston, 2001. The Neuroscientist, Vol. 7, No. 5, 406-418. SAGE Publications Brain Function, Nonlinear Coupling, and Neuronal Transients) that, in addition to the localization and quantitative description of the neuronal electrical activity, the analysis of interactions between different areas of the brains has also become indispensable in both modern brain research and clinical neurology. Thus, in addition to the type of coupling between the areas (linear or non-linear), a particular crucial modern neurological question is also that of the directionality of the coupling. The directionality of the coupling describes which area of the brain is influenced by the activity of another area that is connected thereto.

Despite progress with respect to the design of the phantoms and the modeling of the measured data, the problem is that the quality of the overall measurement systems described in the prior art remains insufficient for such complex questions, and in particular for the description of the non-linear transfer function of a measurement system.

SUMMARY OF THE INVENTION

It is therefore the object of the invention to provide a phantom that does not exhibit the disadvantages found in the prior art, and which thus further allows complex problems, such as the description of non-linear transfer functions in the measurement system, to be analyzed.

The object is achieved by a phantom according to the main claim and by a method according to the additional independent claim. Advantageous embodiments will be apparent from the claims that refer to these two claims, respectively.

The phantom comprises at least one first means for generating at least one dipole. It is characterized by at least one second means for actuating the at least one first means in a non-electrical manner.

Advantageously, this results in the dipole being generated by the first means without interference, since in contrast to phantoms according to the prior art, electrical supply lines are foregone.

Within the context of the invention, it was recognized that interference in the form of undesired electromagnetic fields cannot be avoided, even by way of highly complex shielding of the coaxial cables. Interference from electrical supply lines distorts the electromagnetic fields generated by the dipoles, even with the highest quality shielding, and makes the exact localization of these fields and the estimation of the intensities thereof more difficult.

Within the context of the invention, it was furthermore found that this interference increases with the number and intensity of the simultaneously generated dipoles on the supply lines, so that the accuracy of the required quality estimation is impaired in terms of localization, quantitative description, and reconstruction of the complex temporal dynamics of the current density distributions. As a result, when simultaneously actuating the dipoles via the electrical supply lines in the phantom, the detection sensitivity of the measurement system can no longer be determined, particularly with respect to weak non-linear couplings, with or without temporally alternating directionality between differently localized dipoles. The signals measured by the SQUIDs of a magnetoencephalograph, or by the electrodes of an electroencephalograph, can therefore no longer be uniquely associated with the specific dipoles at the defined measurements sites in the phantom.

Within the context of the invention, it was further found that algorithms used to analyze the type and the direction of the coupling usually also prove to be highly sensitive to metrological noise, such as that caused directly by the procedure described above. For these reasons, the simultaneous generation of different dipoles having non-linearly coupled signals with known directionality, and the subsequent comparison of these signals to the signal lines that were reconstructed based on the back calculation algorithms, have heretofore been unsatisfactory, but are nonetheless indispensable for the evaluation of the measurements.

Thus, complex questions cannot be pursued.

Advantageously, the phantom according to the invention can now be used to generate complex actuating patterns without interference, whereby the aforementioned complex questions regarding the type of coupling and directionality can henceforth be pursued. Thus, analysis of the non-linear transfer functions of the measurement system is possible using the phantom according to the invention.

Particularly advantageously, the claimed non-electrical actuation of a plurality of first means generates the desired dipole fields exclusively at defined, well-known physical measurement sites, without interference from supply lines, which made localization, or determination of the intensity or reciprocal action of the dipoles with respect to each other more difficult.

Due to the design principles, electromagnetic interference, which in phantoms according to the prior art is caused by supplying energy via the supply lines, is eliminated in the phantom according to the invention.

In an advantageous embodiment of the invention, the phantom comprises a second means having at least one light source. Actuation of a first means is then carried out by way of light.

A second means, for this purpose, advantageously comprises at least one light-emitting diode as the light source. It is conceivable to provide a laser as a component of a second means, in place of a light-emitting diode. A light-emitting diode is particularly advantageous because it is inexpensive and can be actuated in a simple manner by a voltage source.

In a further embodiment of the invention, a second means further comprises at least one optical waveguide as a non-electrical supply line for actuating at least one first means. The light from the one or more light sources is coupled into the optical waveguide or optical waveguides.

The light enters an optical waveguide associated with the light source as a non-electrical supply line for actuating the first means, for the local generation of the dipole. A light source and an optical waveguide associated with this light source together advantageously form a second means for actuating a first means.

However, it is also conceivable that the light of a light source is simultaneously coupled into a plurality of optical waveguides for actuating a plurality of first means.

In particular, a light-emitting diode and an optical waveguide associated with this light-emitting diode are advantageously inexpensive and can be matched to each other spatially and functionally in a simple manner.

According to one particularly advantageous embodiment of the invention, a convex lens is preferably affixed to the open end of the optical waveguide to diffuse emitted light.

The lens advantageously again diffuses the focused light emitted by the optical waveguide so that this irradiates a first means for generating the dipole and allows for a high current yield by the first means.

In order to be able to use and match the various components of a second means, it is a prerequisite that a sufficiently strong electrical current for generating a sufficiently strong dipole (~200 nAm) can be generated via the non-electrical supply line.

In a further preferred embodiment of the invention, the light emitted by the optical waveguide strikes the light-absorbing part of at least one photodiode serving as the first means.

Locally, the photodiode generates an electrical current or dipole in the phantom. The photodiode is preferably shielded. This simplifies the shapes of the fields that are generated.

At least one photodiode forms a measurement site in the phantom. As a first means, the photodiode advantageously comprises either a wire for generating an electrical dipole, or a coil for generating a magnetic dipole. The resistance of the wire or coil is known.

These measures produce flexibility in terms of the design of the first means. As a result, a plurality of dipoles having different qualities can be generated. This in turn allows even more complex questions of the type mentioned above to be handled.

Thus, according to the invention, both current dipoles and magnetic dipoles can advantageously be generated, depending on the type of the phantom and depending on the intended purpose.

In a further particularly preferred embodiment of the invention, exactly two, or exactly three, photodiodes form a measurement site in the phantom.

Several photodiodes per measurement site are, in particular, disposed at right angles and as close as possible, for example at a distance of 2 to 5 millimeters, to each other. Due to the superimposition of the generated dipole fields, this arrangement allows for the simulation of an electrical or magnetic dipole having any arbitrary orientation within a plane, in the case of two photodiodes per measurement site, or with three photodiodes per measurement site, even within space.

Notably, it is possible to simulate a dipole having an orientation that can be varied in time and/or space by way of suitable actuation of the photodiodes. Each photodiode for each measurement site is preferably actuated by a dedicated optical waveguide.

If two photodiodes are provided per measurement site, a dipole having an orientation that can be varied with respect to time can be simulated within a plane. If exactly three photodiodes are provided per measurement site in the phantom, it is possible to simulate a dipole having an orientation that can also be varied with respect to time and/or space.

These enhancements optimize the direction-specific calibration of the measurement system. In this regard, the embodiment having three photodiodes per measurement site in the phantom is preferred, because it provides maximum flexibility. However, as differs from the prior art, even the embodiment having two photodiodes allows the quality to be estimated with respect to, for example, the detection of rotating dipoles.

In a further, particularly preferred embodiment of the invention, the at least one photodiode may comprise areas for the absorption of light having different wavelengths. Such two-color photodiodes are provided with two current outputs, which are each excited by light of different wavelengths.

As a result, a dipole having temporally alternating algebraic signs (current direction) can advantageously be generated, even with only one photodiode as a first means. The dipole is generated by the temporally coordinated coupling of light having different wavelengths into the optical waveguide associated with this photodiode.

In this way, two electrical currents that are independent from each other can advantageously be generated using one optical waveguide, because the optical waveguide can irradiate both regions of the photodiode.

In a further embodiment, these currents are oriented antiparallel to each other and adjoin each other very closely (for example, ~1 mm). In this way, a dipole having temporally alternating algebraic signs can be actuated using an optical waveguide.

In a further embodiment of the invention, the phantom according to the invention comprises a number of second means for actuating the first means that is identical to the number of the first means for generating the dipoles. Each first means, such as a photodiode, is then associated with a second means. This relates in particular to optical waveguides and light-emitting diodes that are matched to each other in order to form second means, which are oriented at the photodiodes associated with them as first means so that they generate the dipoles by way of irradiation of the photodiodes. The phantom, as such, however, is in no way limited to this embodiment alone.

Preferably, a plurality of such first and second means that are matched to each other are implemented in the phantom. The phantom is advantageously configured in a head shape.

A voltage source may be provided, which supplies the light sources with suitable voltage. The voltage source may be part of a dipole driver.

If several electrical and/or magnetic dipoles are actuated simultaneously, the phantom may advantageously comprise a controller. This controller may be configured so that it can generate several voltages at a time. As an alternative, it is also possible that a correspondingly high number of controllers be provided.

The phantom according to the invention enables, without interference, the generation of many different dipoles at the same time at defined (measurement) sites inside the phantom. When using actuating signals having defined coupling, for example non-linear coupling and directionality, the extent to which these coupling properties are passed on in a distorted or noisy manner by the measurement system, magnetoencephalograph, or electroencephalograph used can be determined.

Thus, the coupling intensity and coupling type can advantageously even be detected by the measurement system. For this detection, the complete absence of interference fields, such as occur in phantoms according to the prior art, is an indispensible prerequisite. The corresponding results are used for calibrating the measurement system, but can also be used for the optimization thereof. Likewise, error in the spatial localization of simultaneous sources can be quantified using the corresponding back calculation algorithms.

A method in which a phantom according to the invention can advantageously be employed is used for the quantitative and/or qualitative determination of the non-linear transfer function of a measurement system, such as that of a magnetoencephalograph or an electroencephalograph. For this purpose, the following steps are performed:

the dipoles in a phantom are generated via non-electrical supply lines using signals,
the sensors of the measurement system sense the electromagnetic fields generated by the dipoles,
the current density is reconstructed from the sensor data,
the non-linear transfer function of the measurement system is determined.

Preferably, optical waveguides are selected as the non-electrical supply lines. Signals which are coupled to each other in a defined manner, particularly in a non-linear manner, reach the optical waveguides. The dipoles are then generated at different measurement sites in the phantom.

Using the algorithm, based on the sensor data, the current density vector is reconstructed in the voxels captured by the measurement system. It is also possible to use different algorithms for the reconstruction. Finally, the non-linear transfer function of the measurement system is determined from the comparison of the back-calculated data with known signals for excitation of the dipoles.

A further method in which the phantom may be employed is used for checking or determining head position during and/or after a magnetoencephalograph measurement. For this purpose, optically actuated magnetic first means for generating the dipoles are affixed to designated positions of the head and, at specific times, magnetic dipoles having a precisely known magnitude are generated. The head position is determined by reconstructing the coil position based on the magnetoencephalograph measurement. As differs from the prior art, optical actuation avoids electromagnetic interference resulting from the supply of energy, which would otherwise be present. Advantageously, motion artifacts are avoided by the non-electrical actuation.

The invention will be explained in more detail below with reference to one embodiment and the attached figures.

DESCRIPTION OF THE PREFERRED EMBODIMENTS

Figure 1:
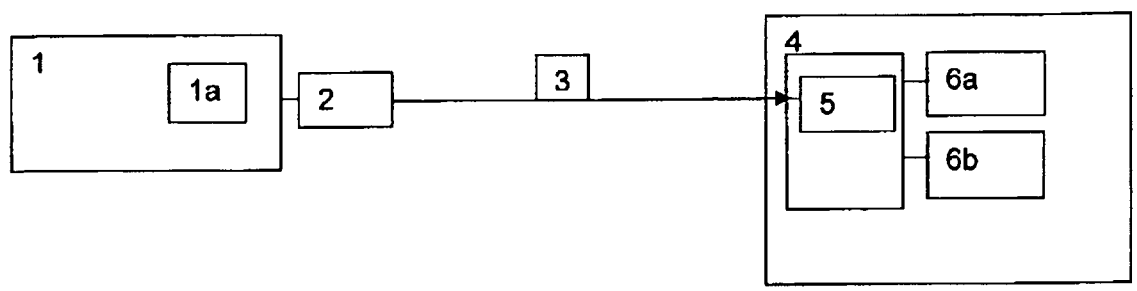
FIG. 1 is a schematic illustration of the principle of actuating a first means for generating a dipole using a second means. A photodiode 5 is provided as the first means, and a unit comprising a light-emitting diode 2 and an associated optical waveguide 3 is provided as the second means.

A white light-emitting diode 2 having high luminous intensity, such as a 240 lumen Lumiled LUXEON LED, is actuated by a controllable analog voltage source 1a and, via an optical waveguide 3, irradiates the light-absorbing part of a photodiode 5. A Siemens BPW 34 is provided as the photodiode.

A controller 1 for controlling the voltage of a plurality of such light-emitting diodes 2, such as a computer, is provided. The computer 1 comprises the voltage source 1a, which in the present example is a digital-to-analog converter.

The photodiode 5 generates the desired current in accordance with the light intensity of the light-emitting diode 2 controlled by the voltage of the voltage source 1a.

The electrical contacts of the photodiode 5 are connected either to a straight wire 6a in order to generate an electrical dipole, or to a wire 6b which is wound in a coil shape in order to generate a magnetic dipole. Such embodiments of the photodiodes are shown in FIGS. 2 to 4.

Figure 2:
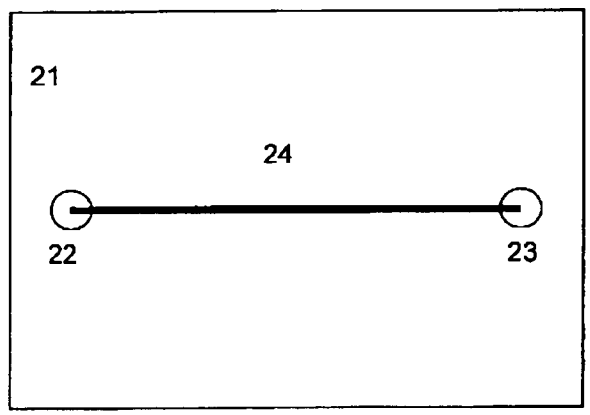
FIG. 2 to FIG. 4 show embodiments of photo diodes for the phantom according to the invention.

In FIG. 2, the electrically positive contact 22 and the electrically negative contact 23 of the photodiode are connected to each other at the back 21 of the photodiode by the electrically conductive wire 24.

Figure 3:
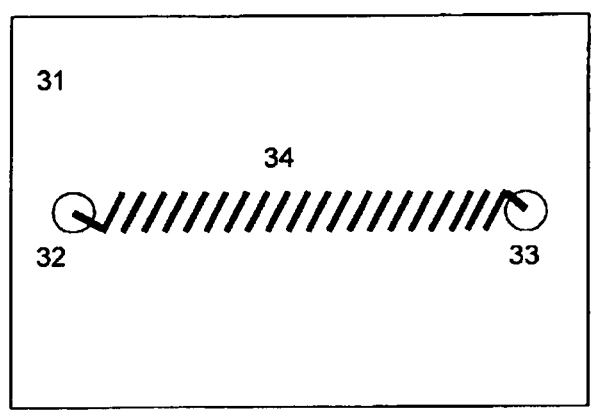

In FIG. 3, the electrically positive contact of the photodiode 32 and the electrically negative contact 33 of the photodiode are connected to each other at the back 31 of the photodiode by the electrically conductive wire 34 wound as a coil having 20 turns.

Figure 4:
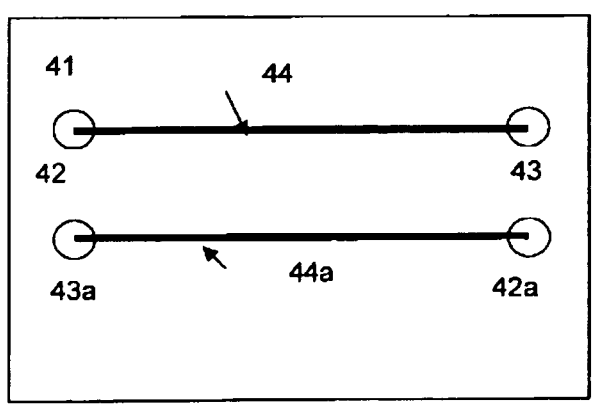

In the case of a two-color diode for the phantom according to the invention, the electrical contacts according to FIG. 4 are positioned and connected to each other so as to generate an electrical dipole. At the back 41 of the photodiode, reference numerals 42 and 43 denote the positive and negative contacts of the electrical output of the two-color photodiode that is part of the first wavelength region. Reference numerals 42a and 43a denote the electrically positive and negative contacts of the electrical output of the two-color photodiode that is part of the second wavelength region. The contacts are connected to each other, in the manner described, by the wires 44 and 44a. Alternatively, wire 44 and/or 44a can also be replaced by a coil, as shown in FIG. 3.

When the resistance is known, the magnetic or electrical dipoles generated by the light can be exactly calculated, in keeping with the designs of these current conductors and the ratio between the applied voltage and the applied current of the photodiode 5, and the time line of the applied voltage, without having to take into consideration any interfering influence from any supply of energy.

The dipoles generated in this way are captured in the measurement region 4 of the respective measurement system, the electroencephalograph or the magnetoencephalograph (see FIG. 1).

It is a matter of course that a plurality of light-emitting diodes 2, optical waveguides 3, and specially configured photodiodes 5 can be used in the phantom, in keeping with the number and type of the dipoles to be generated, and can be connected to the voltage source and/or the controller.

The invention claimed is:

1. A phantom comprising:
   a plurality of dipole generators having defined intensities in defined physical sites; and
   a plurality of actuators that actuate said plurality of dipole generators in a non-electrical manner.

2. The phantom according to claim 1, wherein plurality of actuators comprise at least two light sources.

3. The phantom according to claim 2, wherein each of the at least two light sources comprises a light-emitting diode.

4. A phantom according to claim 1, wherein the plurality of actuators comprise at least two optical waveguides.

5. A phantom according to claim 1, wherein the plurality of dipole generators comprise at least two photodiodes.

6. A phantom according to claim 5,
   wherein each photodiode of the at least two photodiodes is configured as one of said defined physical sites.

7. A phantom according to claim 5, wherein each photodiode of the at least two photodiodes is configured to comprise a plurality of regions for absorbing light at differing wavelengths.

8. A phantom according to claim 5, wherein each two photodiodes of the at least two photodiodes are configured as one of said defined physical sites.

9. A phantom according to claim 5, wherein said at least two photodiodes comprise at least six photodiodes, and wherein each three photodiodes of the at least six photodiodes are configured as one of said defined physical sites.

10. A phantom for generating dipoles having defined intensities in defined physical sites, comprising:
    a plurality of input signals;
    a plurality of dipole generators generating a plurality of dipoles, each one dipole generator of said plurality of dipole generators generating a subset of the plurality of dipoles at a physical site among said plurality of physical sites over time at defined intensities in response to a corresponding input signal among said plurality of input signals;
    a corresponding plurality of input actuators respectively applying said plurality of input signals to said plurality of generators; and
    a controller that controls said plurality of actuators to determine said plurality of input signals.

11. The phantom of claim 10, wherein each one dipole generator among the plurality of dipole generators comprises a light sensor and a wire;
    wherein each one input actuator among said plurality of input actuators comprises a light emitter;
    wherein said controller controls emission of light from the light emitter; and
    wherein the light sensor responds to the emitted light to generate said respective input signal.

12. The phantom of claim 11, wherein said light sensor comprises a photodiode.

13. The phantom of claim 11, wherein said light emitter comprises a light-emitting diode and an optical waveguide, said optical waveguide being a light transmission medium for light to travel from the light emitter to a corresponding light sensor.

14. The phantom of claim 11, wherein for said each one dipole generator there is a corresponding one input actuator among said plurality of input actuators.

15. The phantom of claim 11, wherein said plurality of dipole generators and said plurality of input actuators correspond at a ratio of 2:1 so that for each one input actuator among said plurality of input actuators there are two dipole generators among said plurality of corresponding dipole generators, and said each one input actuator generates a common input signal for said corresponding two dipole generators.

16. The phantom of claim 11, wherein said plurality of dipole generators and said plurality of input actuators correspond at a ratio of 3:1 so that for each one input actuator among said plurality of input actuators there are three dipole generators among said plurality of corresponding dipole generators, and said each one input actuator generates a common input signal for said corresponding three dipole generators.

\* \* \* \* \*